United States Patent [19]
Putzer

[11] Patent Number: 6,022,338
[45] Date of Patent: Feb. 8, 2000

[54] ABSORBENT ARTICLE HAVING A MULTILAYERED CONTAINMENT BARRIER

[75] Inventor: Melissa Christine Putzer, Oshkosh, Wis.

[73] Assignee: Kimberly-Clark Worldwide, Inc., Neenah, Wis.

[21] Appl. No.: 08/974,171

[22] Filed: Nov. 19, 1997

[51] Int. Cl.[7] .................................................... A61F 13/15
[52] U.S. Cl. ....................................... 604/385.1; 604/378
[58] Field of Search ............................. 604/385.1, 385.2, 604/378

[56] References Cited

U.S. PATENT DOCUMENTS

| | | |
|---|---|---|
| 810,122 | 1/1906 | Green . |
| 810,123 | 1/1906 | Green . |
| 810,125 | 1/1906 | Green . |
| 810,130 | 1/1906 | Green . |
| 2,917,049 | 12/1959 | Delaney .................................. 604/378 |
| 3,885,568 | 5/1975 | Schaar . |
| 4,257,418 | 3/1981 | Hessner . |
| 4,662,877 | 5/1987 | Williams . |
| 4,681,577 | 7/1987 | Stern et al. . |
| 4,704,116 | 11/1987 | Enloe . |
| 4,762,521 | 8/1988 | Roessler et al. . |
| 4,778,459 | 10/1988 | Fuisz . |
| 4,798,603 | 1/1989 | Meyer et al. . |
| 4,804,379 | 2/1989 | Toth et al. . |
| 4,892,536 | 1/1990 | DesMarais et al. . |
| 4,950,262 | 8/1990 | Takagi . |
| 4,990,147 | 2/1991 | Freeland . |
| 5,062,840 | 11/1991 | Holt et al. . |
| 5,069,678 | 12/1991 | Yamamoto et al. ................. 604/385.1 |
| 5,171,236 | 12/1992 | Dreier et al. . |
| 5,176,668 | 1/1993 | Bernardin . |
| 5,176,672 | 1/1993 | Bruemmer et al. . |
| 5,192,606 | 3/1993 | Proxmire et al. . |
| 5,204,997 | 4/1993 | Suzuki et al. ............................... 2/400 |

(List continued on next page.)

FOREIGN PATENT DOCUMENTS

| | | |
|---|---|---|
| 0 631 767 A1 | 1/1995 | European Pat. Off. . |
| 0 692 231 A1 | 1/1996 | European Pat. Off. . |
| 0 716 842 A1 | 6/1996 | European Pat. Off. . |
| 2 740 929 A3 | 11/1996 | European Pat. Off. . |
| 94/9179 | 11/1994 | South Africa . |
| 94/9262 | 11/1994 | South Africa . |
| 2 284 537 | 6/1995 | United Kingdom . |
| 2 284 538 | 6/1995 | United Kingdom . |
| 2 284 550 | 6/1995 | United Kingdom . |
| 2 287 393 | 9/1995 | United Kingdom . |
| 2 294 398 | 5/1996 | United Kingdom . |
| WO 96/01609 | 1/1996 | WIPO . |

OTHER PUBLICATIONS

Patent Cooperation Treaty Search Report from the International Search Authority, International Application No. PCT/US 98/24546 dated Mar. 29, 1999.

*Primary Examiner*—John Weiss
*Assistant Examiner*—Dennis Ruhl
*Attorney, Agent, or Firm*—Jeffrey B. Curtin

[57] ABSTRACT

An absorbent article includes at least one multilayered containment barrier which is configured to inhibit the flow of body exudates along the surface of the absorbent article. The containment barrier includes multiple layers of material. Each of the layers defines an inner edge which remains at least partially unattached to the other layers to allow the body exudates to flow into an area between the layers in use for improved containment and absorption of exudates. In a particular embodiment, the absorbent article may include a pair of such containment barriers which are laterally spaced apart to provide a void space between the wearer's buttocks and the surface of the absorbent article for containing body exudates. In such a configuration, the absorbent article may further include a pair of longitudinally extending containment flaps located on the side edges of the article laterally outwards from the containment barriers for improved containment Alternatively, the containment barriers may be located between the topsheet layer and absorbent body of the absorbent article. In such a configuration, the topsheet layer defines an opening which is located at least partially over the containment barriers to receive fecal exudates.

20 Claims, 4 Drawing Sheets

U.S. PATENT DOCUMENTS

| | | |
|---|---|---|
| 5,207,663 | 5/1993 | McQueen . |
| 5,269,775 | 12/1993 | Freeland et al. . |
| 5,281,208 | 1/1994 | Thompson et al. . |
| 5,300,053 | 4/1994 | Genaro . |
| 5,304,159 | 4/1994 | Tanji et al. . |
| 5,304,160 | 4/1994 | Igaue et al. . |
| 5,306,266 | 4/1994 | Freeland . |
| 5,330,459 | 7/1994 | Lavon et al. . |
| 5,330,598 | 7/1994 | Erdman et al. . |
| 5,344,516 | 9/1994 | Tanji et al. . |
| 5,356,405 | 10/1994 | Thompson et al. . |
| 5,366,453 | 11/1994 | Zehner et al. . |
| 5,391,160 | 2/1995 | Runeman et al. . |
| 5,409,476 | 4/1995 | Coates . |
| 5,417,680 | 5/1995 | Kimura et al. . |
| 5,439,458 | 8/1995 | Noel et al. . |
| 5,439,459 | 8/1995 | Tanji et al. . |
| 5,451,442 | 9/1995 | Pieniak et al. . |
| 5,509,915 | 4/1996 | Hanson et al. . |
| 5,514,121 | 5/1996 | Roe et al. ............................ 604/385.1 |
| 5,558,660 | 9/1996 | Dreier . |
| 5,575,785 | 11/1996 | Gryskiewicz et al. ................ 604/385.2 |
| 5,584,827 | 12/1996 | Korteweg et al. ....................... 604/369 |
| 5,827,259 | 10/1998 | Laux et al. ............................ 604/385.2 |

ABSORBENT ARTICLE HAVING A MULTILAYERED CONTAINMENT BARRIER

BACKGROUND OF THE INVENTION

1. Field of the Invention

The present invention relates to an absorbent article for absorbing body fluids and exudates, such as urine and fecal material. More particularly, the present invention relates to absorbent garments, such as disposable diapers and adult incontinence garments, which are configured to collect and contain fecal material and avoid leakage.

2. Description of the Related Art

Conventional absorbent articles, such as disposable diapers, employ absorbent materials located between a liquid pervious topsheet and a liquid impermeable backsheet to absorb body exudates. Such conventional absorbent articles have also typically included elasticized waistbands and leg cuffs to help reduce the leakage of body exudates.

However, many of such conventional absorbent articles have not been completely satisfactory. For example, many conventional absorbent articles have not completely contained the body exudates within the article during use thereby undesirably resulting in leakage which has soiled the clothes of the wearer. This leakage problem has been particularly evident in the leg and waist regions of such absorbent articles when runny or watery fecal material has been excreted by the wearer during use. Typically, the runny or watery fecal material has been forced laterally and longitudinally outwards from the crotch of the article towards the leg and waist openings in the article due to the forces exerted by the wearer. Such problems are magnified when the wearer is particularly active and continually exerts pressure on the crotch area of the article. The leakage problem has also occurred because such fecal material, which has an affinity for the skin, has traveled along the skin of the wearer and has not been sufficiently contained and controlled within the absorbent article.

Some conventional absorbent articles have included elasticized components and containment or barrier flaps at the leg and waist regions of the article to reduce such leaks. However, such elasticized components and containment flaps have not always completely eliminated leakage from the leg regions of such articles. For example, exudates such as runny fecal material have remained on and been transferred along the skin of the wearer until they escape through small openings between the containment flaps and the body of the wearer. Such openings between the body of the wearer and the containment flaps have been caused by improper fit of the article about the wearer and the movements of the wearer during use. Moreover, such containment flaps have typically not been very resistant to compressive forces and have readily collapsed under the weight of or forces exerted by the wearer. Such collapsing has undesirably allowed the wearers body to contact the bodyside liner of the article during use which has forced any fecal exudates out of the crotch portion.

As a result, although such leg elastics and containment flaps have improved the performance of such articles, there remains a need to further reduce the number of leaks of fecal material from the leg and waist regions of such absorbent articles.

SUMMARY OF THE INVENTION

In response to the difficulties and problems discussed above, a new disposable absorbent article which includes at least one multilayered three-dimensional containment barrier for containing and stopping the flow of body exudates and, in particular, runny fecal material has been discovered.

As used herein, the term "compression resistance" refers to the compression resistance value determined according to the Compression Resistance Test set forth below.

As used herein, the term "multilayered" refers to at least three distinct layers of material, desirably at least about 5 layers of material, and more desirably at least about 8 layers of material.

In one aspect, the present invention relates to a disposable absorbent article which includes at least one multilayered containment barrier. The containment barrier is located adjacent an edge of the absorbent article to inhibit the flow of body exudates. The containment barrier includes multiple layers of material wherein each of the layers defines an inner edge which remains at least partially unattached to the other layers to allow the body exudates to flow into an area between the layers in use. In a particular embodiment, each of the layers defines an unattached width which is at least about 10 percent of a width of the containment barrier.

In another aspect, the present invention relates to a disposable absorbent article having a front waist section, a rear waist section, an intermediate section which interconnects the front and rear waist sections, a pair of longitudinally opposed end edges, and a pair of laterally opposed side edges. The article includes a backsheet layer, a liquid permeable topsheet layer which is connected in superposed relation to the backsheet layer, an absorbent body which is located between the topsheet layer and the backsheet layer, and a pair of longitudinally extending, multilayered containment barriers. The containment barriers are located in a laterally spaced apart relation on the topsheet layer of the absorbent article and are configured to provide a void space between a wearer's buttocks and the topsheet layer for containing body exudates. Each of the containment barriers includes at least 3 layers of material. In a particular embodiment, each of the layers of the containment barriers defines an inner edge which remains at least partially unattached to the other layers to allow the body exudates to flow into an area between said layers in use. The containment barrier may further define a compression resistance of at least about 50 percent.

In yet another aspect, the absorbent article may further comprise a pair of longitudinally extending containment flaps which are located along the side edges of the absorbent article laterally outwards from the containment barriers. The containment flaps define an attached edge which is at least partially attached to the side edges of the absorbent article, a free edge which remains unattached to the side edges in at least the intermediate section of the absorbent article, and at least one elastic member which is configured to maintain the free edge in a generally perpendicular, spaced away relationship from the side edge of the absorbent article in the intermediate section.

In still another aspect, the present invention relates to a disposable absorbent article having a front waist section, a rear waist section, an intermediate section which interconnects the front and rear waist sections, a pair of longitudinally opposed end edges, and a pair of laterally opposed side edges. The article includes a backsheet layer, a topsheet layer which is connected in superposed relation to the backsheet layer and which defines an opening therein for receiving fecal exudates, an absorbent body which is located between the topsheet layer and the backsheet layer, and a pair of longitudinally extending, multilayered containment barriers. The containment barriers are located in a laterally spaced apart relation between the absorbent body and the topsheet layer of the absorbent article and are configured to provide a void space between a wearer's buttocks and the absorbent body of the absorbent article for containing body exudates. Each of the containment barriers includes multiple layers of material each of which defines an inner edge which remains at least partially unattached to the other layers to allow the body exudates to flow into an area between the layers in use. In a particular embodiment, the topsheet layer includes an elastic member adjacent at least a portion of each lateral edge of the opening to maintain the opening in contact with the wearer's buttocks in use.

The various aspects of the present invention can advantageously provide an absorbent article which effectively absorbs and contains body exudates. In particular, the present invention includes at least one multilayered containment barrier which reduces the flow of body exudates. For example, the absorbent article may include a pair of such containment barriers along it's longitudinal side margins. The layers of the containment barriers remain at least partially unattached to each other such that exudates may flow between the layers for improved performance. The containment barriers may also be compression resistant to space the wearer's body from the absorbent body of the absorbent article to provide a void space for containing the body exudates. As a result, the absorbent articles of the various aspects of the present invention have reduced leakage when compared to conventional absorbent articles which results in improved consumer preference.

BRIEF DESCRIPTION OF THE DRAWINGS

The invention will be more fully understood and further advantages will become apparent when reference is made to the following detailed description of the invention and the accompanying drawings, in which.

DETAILED DESCRIPTION OF THE INVENTION

The following detailed description will be made in the context of a disposable diaper article which is adapted to be worn by infants about the lower torso. It is readily apparent, however, that the absorbent article of the present invention would also be suitable for use as other types of absorbent articles, such as feminine care pads, incontinence garments, training pants, and the like. In addition, the invention will be described in the context of its various configurations. It should be appreciated that alternative arrangements of the invention can comprise any combination of such configurations.

With reference to FIGS. 1–4, an integral absorbent garment article, such as the disposable diaper 20, generally defines a front waist section 22, a rear waist section 24, an intermediate section 26 which interconnects the front and rear waist sections, a pair of laterally opposed side edges 28, and a pair of longitudinally opposed end edges 30. The front and rear waist sections include the general portions of the article which are constructed to extend substantially over the wearers front and rear abdominal regions, respectively, during use. The intermediate section of the article includes the general portion of the article which is constructed to extend through the wearers crotch region between the legs. The opposed side edges 28 define leg openings for the diaper and generally are curvilinear or contoured to more closely fit the legs of the wearer. The opposed end edges 30 define a waist opening for the diaper 20 and typically are straight but may also be curvilinear.

Figure 1:
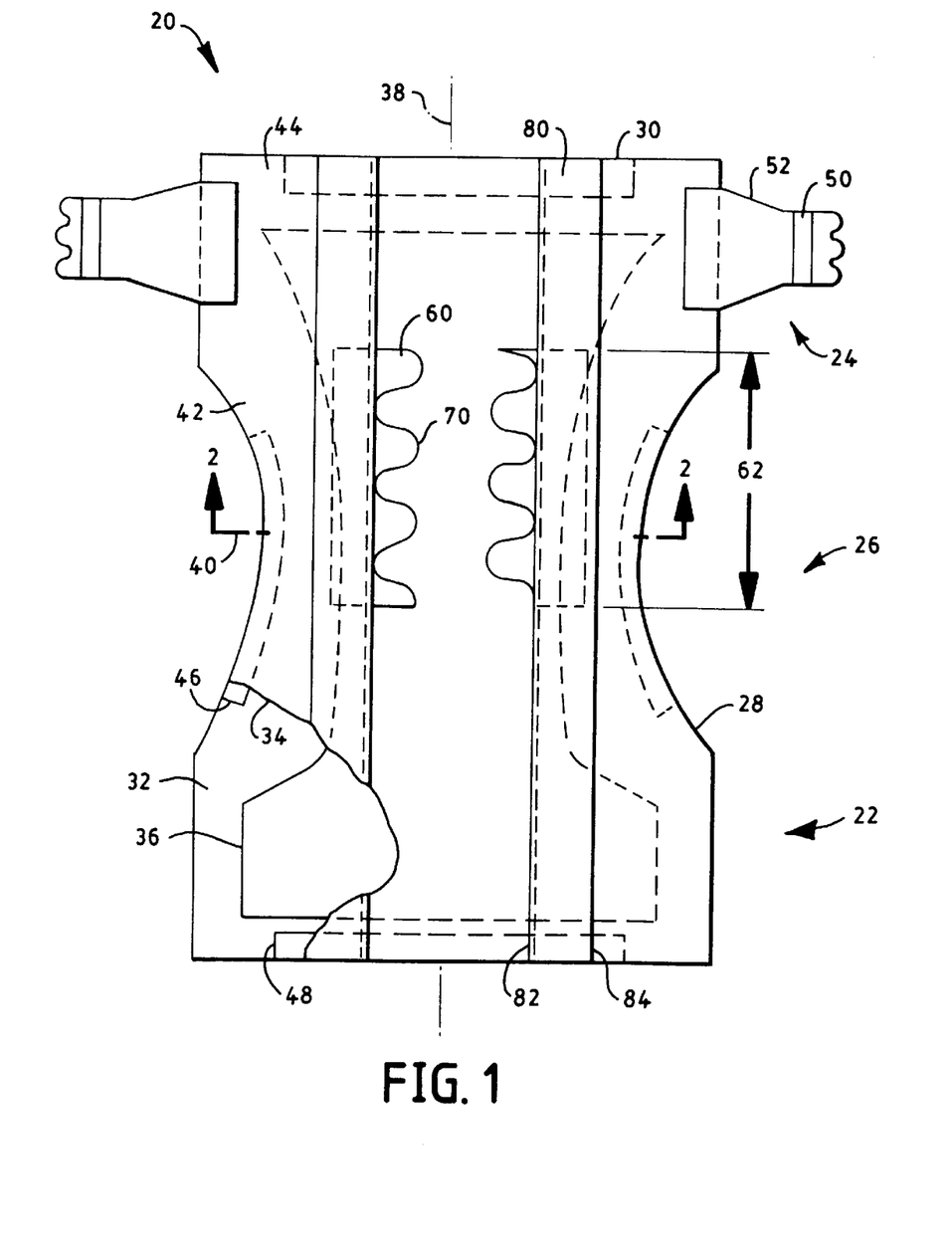
FIG. 1 representatively shows a partially cut away, top plan view of an absorbent article according to one embodiment of the invention.
Figure 2:
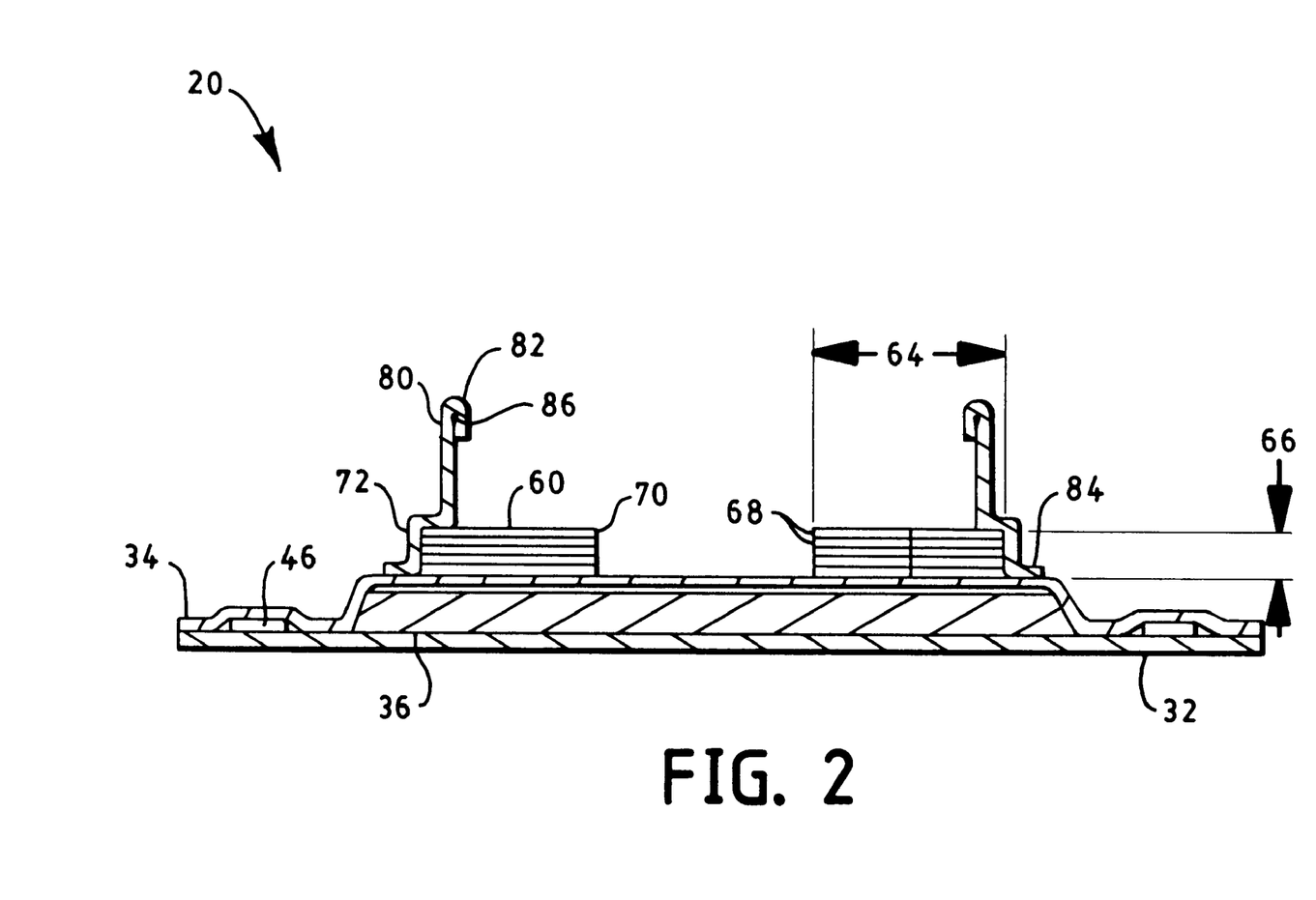
FIG. 2 representatively shows a sectional view of the absorbent article of FIG. 1 taken along line 2—2.
Figure 3:
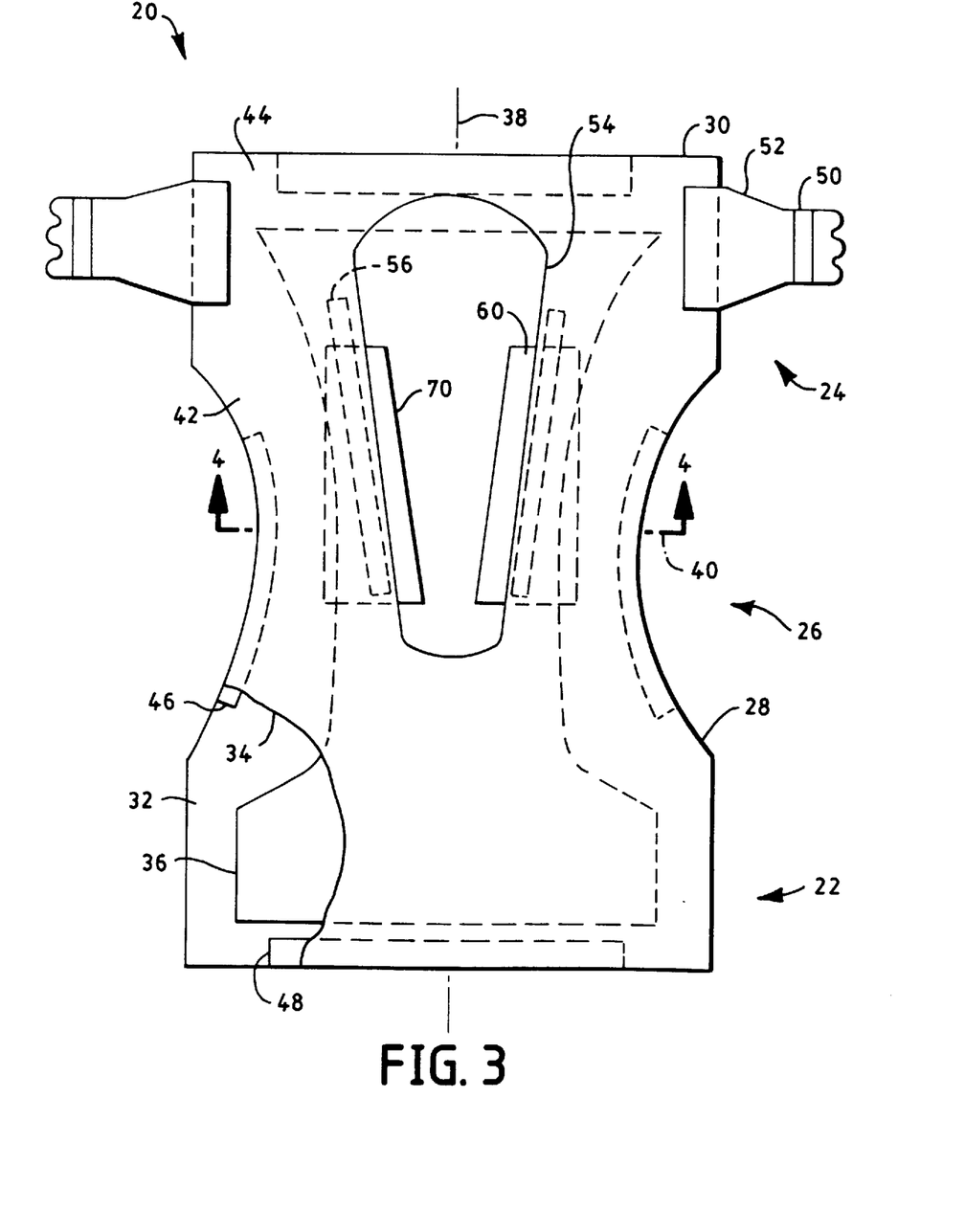
FIG. 3 representatively shows a partially cut away, top plan view of an absorbent article according to another embodiment of the invention.
Figure 4:
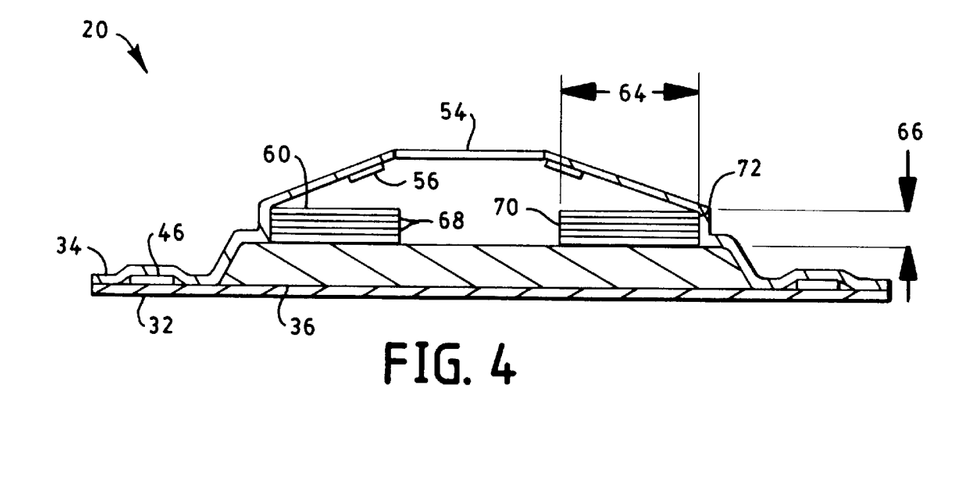
FIG. 4 representatively shows a sectional view of the absorbent article of FIG. 3 taken along line 4—4.

FIGS. 1 and 3 are representative plan views of two variations of diapers 20 according to the present invention in a flat, uncontracted state. FIGS. 2 and 4 show sectional views of the diapers of FIGS. 1 and 3 respectively. In FIGS. 1 and 3, portions of the structure are partially cut away to more clearly show the interior construction of the diaper 20, and the surface of the diaper which contacts the wearer is facing the viewer. The diaper 20 includes a substantially liquid impermeable backsheet 32, a porous, liquid permeable topsheet 34 positioned in facing relation with the backsheet 32, and an absorbent body 36, such as an absorbent pad, which is located between the backsheet and the topsheet. The diaper 20 also defines a longitudinal centerline 38 and a lateral centerline 40. Marginal portions of the diaper 20, such as marginal sections of the backsheet 32, may extend past the terminal edges of the absorbent body 36. In the illustrated embodiment, for example, the backsheet 32 extends outwardly beyond the terminal marginal edges of the absorbent body 36 to form side margins 42 and end margins 44 of the diaper 20. The topsheet 34 is generally coextensive with the backsheet 32 but may optionally cover an area which is larger or smaller than the area of the backsheet 32, as desired.

To provide improved fit and to help reduce leakage of body exudates from the diaper 20, the side margins 42 and end margins 44 of the diaper may be elasticized with suitable elastic members, such as leg elastic members 46 and waist elastic members 48. For example, the leg elastic members 46 may include single or multiple strands of elastic or elastomeric composites which are constructed to operably gather and shirr the side margins 42 of the diaper 20 to provide elasticized leg bands which can closely fit around the legs of the wearer to reduce leakage and provide improved comfort and appearance. Similarly, the waist elastic members 48 can be employed to elasticize the end margins 44 of the diaper 20 to provide elasticized waistbands. The waist elastics are configured to operably gather and shirr the waistband sections to provide a resilient, comfortably close fit around the waist of the wearer.

The elastic members 46 and 48 are secured to the diaper 20 in an elastically contractible condition so that in a normal under strain configuration, the elastic members effectively contract against the diaper 20. For example, the elastic members 46 and 48 may be elongated and secured to the diaper 20 while the diaper is in an uncontracted condition. In FIGS. 1 and 3, the elastic members 46 and 48 are illustrated in their uncontracted, stretched condition for the purpose of clarity. Alternatively, the diaper 20 may include a pair of separate, elasticized and gathered leg gussets (not shown) which are attached to the diaper along the side margins 42 in at least the intermediate section 26 of the diaper 20 to provide elasticized leg cuffs. Such leg gussets may be configured to extend beyond and bridge across the respective concave portion of the side margins 42.

The diaper 20, as representatively illustrated in FIGS. 1 and 3, may further include a pair of fasteners 50 which are employed to secure the diaper 20 about the waist of a wearer. Suitable fasteners 50 include hook-and-loop type fasteners, adhesive tape fasteners, buttons, pins, snaps, mushroom-and-loop fasteners, and the like. A cooperating side panel member 52 can be associated with each fastener and may be constructed to be nonelasticized, or to be elastically stretchable at least along the lateral direction of the diaper 20.

As representatively illustrated in FIGS. 1 and 2, the diaper 20 may also include a pair of elasticized, longitudinally extending containment flaps 80 which are configured to maintain an upright, perpendicular arrangement in at least the intermediate section 26 of the diaper 20 to serve as an additional barrier to the lateral flow of body exudates. The containment flaps include a free edge 82 which remains unattached to the topsheet 34 of the diaper 20 in at least the intermediate section 26 of the diaper and an attached edge 84 which may remain attached to the topsheet 34 over substantially the entire length of the containment flap 80. The containment flaps 80 also include an elastic means 86 which is configured to maintain the free edge 82 spaced away from the topsheet 34 in at least the intermediate section 26 of the diaper 20 to maintain the upright arrangement to provide a barrier against the lateral flow of exudates. Alternatively, as representatively illustrated in FIGS. 3 and 4, the topsheet 34 may be configured to fit closely to the wearers body such that a void space is created between the topsheet 34 and the absorbent body 36 of the diaper 20. In such a configuration, the topsheet 34 includes an opening therein for receiving fecal exudates from the wearer.

The diaper 20 may further include a surge management layer (not shown) positioned between the topsheet 34 and the absorbent body 36 which is configured to efficiently hold and distribute liquid exudates to the absorbent body 36. The surge management layer can prevent the liquid exudates from pooling and collecting on the portion of the diaper positioned against the wearer's skin, thereby reducing the level of skin hydration. Suitable constructions and arrangements of containment flaps and surge management layers are well known to those skilled in the art. Other suitable diaper components may also be incorporated on absorbent articles of the present invention.

The diaper 20, as representatively illustrated in FIGS. 1 and 3, further includes at least one multilayered containment barrier 60 located along an edge of the diaper 20 to contain or absorb at least a portion of the body exudates and reduce the flow of such exudates from the diaper 20. For example, as representatively illustrated in FIGS. 1–5, the diaper 20 may include a pair of such multilayered containment barriers 60 located along the side edges 28 of the diaper 20 in a longitudinally extending manner at least in the intermediate section 26 of the diaper 20 to reduce the lateral flow of exudates out of the diaper 20. In such a configuration, the containment barriers 60 are further configured to provide a void space between the buttocks of the wearer and the absorbent portion of the diaper 20 during use. The void space is configured to contain body exudates and, in particular, fecal exudates until they can be absorbed or desorbed by the absorbent body 36 of the diaper 20.

The diaper 20 may also include at least one multilayered containment barrier 60 located along one of the end edges 30 of the diaper 20 in a laterally extending manner to reduce the longitudinal flow of exudates out of the diaper 20 in a similar manner. Such a laterally extending barrier 60 may otherwise be located adjacent the end edges of the opening 54 illustrated in FIGS. 3 and 4.

The diaper 20 may be of various suitable shapes. For example, the diaper may have an overall rectangular shape, T-shape or an approximately hour-glass shape. In the shown embodiment, the diaper 20 has a generally I-shape. Examples of diaper configurations suitable for use in connection with the instant application and other diaper components suitable for use on diapers are described in U.S. Pat. No. 4,798,603 issued Jan. 17, 1989, to Meyer et al.; U.S. Pat. No. 5,176,668 issued Jan. 5, 1993, to Bemardin; U.S. Pat. No. 5,176,672 issued Jan. 5, 1993, to Bruemmer et at.; U.S. Pat. No. 5,192,606 issued Mar. 9, 1993, to Proxmire et al.; and U.S. Pat. No. 5,509,915 issued Apr. 23, 1986, to Hanson et al., the disclosures of which are herein incorporated by reference to the extent they are consistent herewith. The various aspects and configurations of the invention can provide distinctive combinations of softness, body conformity, reduced red-marking of the wearers skin, reduced skin hydration, and improved containment of body exudates.

The various components of the diaper 20 are integrally assembled together employing various types of suitable attachment means, such as adhesive, sonic bonds, thermal bonds or combinations thereof. In the shown embodiment, for example, the topsheet 34 and backsheet 32 are assembled to each other and to the absorbent body 36 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Similarly, other diaper components, such as the elastic members 46 and 48 and the fasteners 50, may be assembled into the diaper 20 article by employing the above-identified attachment mechanisms.

The backsheet 32 of the diaper 20, as representatively illustrated in FIG. 1, may suitably be composed of a material which is either liquid permeable or liquid impermeable. It is generally preferred that the backsheet 32 be formed from a material which is substantially impermeable to liquids. For example, a typical backsheet can be manufactured from a thin plastic film or other flexible liquid-impermeable material. For example, the backsheet 32 may be formed from a polyethylene film having a thickness of from about 0.012 millimeter (0.5 mil) to about 0.051 millimeter (2.0 mils). If it is desired to present the backsheet with a more clothlike feeling, the backsheet 32 may comprise a polyolefin film having a nonwoven web laminated to the outer surface thereof, such as a spunbond web of polyolefin fibers. For example, a stretch-thinned polypropylene film having a thickness of about 0.015 millimeter (0.6 mil) may have thermally laminated thereto a spunbond web of polypropylene fibers, which fibers have a thickness of about 1.5 to 2.5 denier per filament, which nonwoven web has a basis weight of about 17 grams per square meter (0.5 ounce per square yard). Methods of forming such clothlike backsheets are known to those skilled in the art.

Further, the backsheet 32 may be formed of a woven or nonwoven fibrous web layer which has been totally or partially constructed or treated to impart a desired level of liquid impermeability to selected regions that are adjacent or proximate the absorbent body 36. Still further, the backsheet 32 may optionally be composed of a micro-porous "breathable" material which permits vapors to escape from the absorbent body 36 while still preventing liquid exudates from passing through the backsheet 32. The backsheet 32 typically provides the outer cover of the diaper 20. The backsheet 32 can also be embossed or otherwise provided with a matte finish to provide a more aesthetically pleasing appearance.

The topsheet 34, as representatively illustrated in FIG. 1, suitably presents a bodyfacing surface which is compliant, soft feeling, and nonirritating to the wearers skin. Further, the topsheet 34 may be less hydrophilic than the absorbent body 36, to present a relatively dry surface to the wearer, and may be sufficiently porous to be liquid permeable, permitting liquid to readily penetrate through its thickness. A suitable topsheet 34 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet 34 is suitably employed to help isolate the wearers skin from liquids held in the absorbent body 36.

Various woven and nonwoven fabrics can be used for the topsheet 34. For example, the topsheet may be composed of a meltblown or spunbonded web of polyolefin fibers. The topsheet may also be a bonded-carded web composed of natural and/or synthetic fibers. The topsheet may be composed of a substantially hydrophobic material, and the hydrophobic material may, optionally, be treated with a surfactant or otherwise processed to impart a desired level of wettability and hydrophilicity. In a particular embodiment of the present invention, the topsheet 34 comprises a nonwoven, spunbond, polypropylene fabric composed of about 2.8–3.2 denier fibers formed into a web having a basis weight of about 20 grams per square meter and a density of about 0.13 gram per cubic centimeter. The fabric may be surface treated with about 0.28 weight percent of a surfactant commercially available from the Rohm and Haas Co. under the trade designation Triton X-102. The surfactant may be applied by any conventional means, such as spraying, printing, brush coating or the like. The surfactant may be applied to the entire topsheet 34 or may be selectively applied to particular sections of the topsheet 34, such as the medial section along the longitudinal centerline of the diaper, to provide greater wettability of such sections.

The absorbent body 36 of the diaper 20, as representatively illustrated in FIG. 1, may suitably comprise a matrix of hydrophilic fibers, such as a web of cellulosic fluff, mixed with particles of a high-absorbency material commonly known as superabsorbent material. In a particular embodiment, the absorbent body 36 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. The fluff and superabsorbent particles may also be selectively placed into desired zones of the absorbent body 36 to better contain and absorb body exudates. The concentration of the superabsorbent particles may also vary through the thickness of the absorbent body 36. Alternatively, the absorbent body 36 may comprise a laminate of fibrous webs and superabsorbent material or other suitable means of maintaining a superabsorbent material in a localized area.

The absorbent body 36 may have any of a number of shapes. For example, the absorbent core may be rectangular, I-shaped, or T-shaped. It is generally preferred that the absorbent body 36 be narrower in the crotch area than in the front or rear portions of the diaper 20. The size and the absorbent capacity of the absorbent body 36 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va. and DOW DRYTECH 2035LD polymer available from Dow Chemical Co. located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on total weight of the absorbent body 36.

Optionally, a substantially hydrophilic tissue wrapsheet (not illustrated) may be employed to help maintain the integrity of the airlaid fibrous structure of the absorbent body 36. The tissue wrapsheet is typically placed about the absorbent body over at least the two major facing surfaces thereof and composed of an absorbent cellulosic material, such as creped wadding or a high wet-strength tissue. In one aspect of the invention, the tissue wrapsheet can be configured to provide a wicking layer which helps to rapidly distribute liquid over the mass of absorbent fibers comprising the absorbent body. In another aspect of the invention, the wrapsheet material on one side of the absorbent fibrous mass may be bonded to the wrapsheet located on the opposite side of the fibrous mass.

The diaper 20 of the present invention further includes at least one multilayered containment barrier 60. For example, as representatively illustrated in FIGS. 1–5, the diaper 20 may include a pair of such multilayered containment barriers 60 which are positioned in a laterally spaced apart relation along the side edges 28 of the diaper 20. In such a configuration, the containment barriers 60 are configured to provide a seal with the wearer's buttock to help reduce leaks along the side edges 28 of the diaper 20 by preventing the lateral flow of fecal exudates. The diaper 20 of the present invention may otherwise or further include at least one such multilayered containment barrier 60 along at least one of the end edges 30 of the diaper 20. For example, in a particular embodiment, the diaper 20 may include multilayered containment barriers 60 along both side edges 28 and end edges 30 of the diaper 20.

The individual layers 68 of the containment barriers 60 are configured to contain or absorb at least a portion of the body exudates within or between each layer. In the illustrated embodiments, the layers 68 of the containment barrier 60 are configured in a parallel relationship with the bodyfacing surface of the diaper 20. However, it is also contemplated that such layers 68 could be oriented in a perpendicular relationship with the bodyfacing surface of the diaper 20. The layered configuration of the containment barriers 60 also improves the transfer of body exudates by allowing movement of the exudates between the layers in a longitudinal direction. As a result, the use of such multilayered containment barriers in the diaper 20 of the different aspects of the present invention can result in improved absorption and containment of body exudates when compared to single layered dams or barriers.

Further, the containment barriers 60 may be at least partially resistant to compression to provide a void space between the containment barriers 60, the wearer's buttocks and the topsheet 34 of the diaper 20 in use. The void space is configured to receive and contain fecal exudates. At least a portion of the fecal exudates may then be absorbed or desorbed by the absorbent body 36 and/or the individual layers of the containment barriers 60. Desirably, the containment barriers 60 are configured to contain substantially all of the solid fecal exudates in the target zone of the diaper 20. As used herein, the term "target zone" refers to that portion of the diaper 20 which is configured to directly receive the insult of fecal exudates from the wearer and generally is located in the crotch portion of the diaper 20. In particular, the target zone may extend from about 5 to about 10 centimeters in length with about one third of it's length extending longitudinally from the lateral centerline 40 of the diaper towards the front waist section 22 of the diaper 20 and the remainder extending longitudinally towards the rear waist section 24 of the diaper 20.

In the embodiments illustrated in FIGS. 1 and 2, two containment barriers 60 are positioned on the bodyfacing surface of the topsheet 34 of the diaper 20 in a laterally spaced apart relationship. The containment barriers 60 may remain substantially unattached to the topsheet 34 or may be attached to the topsheet 34 using conventional means described above such as adhesive. Desirably, the containment barriers 60 are secured to the topsheet 34 in a manner which stabilizes the barriers 60 and maintains the barriers 60 in an upright position during use. Alternatively, as representatively illustrated in FIGS. 3 and 4, the containment barriers 60 may be located between the topsheet 34 and the absorbent body 36 of the diaper 20. In such an arrangement, the diaper 20 may include an additional layer or sheet of material (not illustrated) between the containment barriers 60 and the absorbent body 36. Such a layer may be provided by materials known to those skilled in the art such as those described above as being suitable for use as the topsheet 34 of the diaper 20.

Thus, in the illustrated embodiments, the multilayered containment barriers 60 are located along the side edges 28 of the diaper 20 in the intermediate section 26 of the diaper 20 and generally extend in the longitudinal direction. Desirably, the containment barriers 60 are located on the side edges 28 of the diaper in at least the target zone of the diaper. In particular, the containment barriers 60 may be located on the diaper 20 such that about one third of their length 62 extends longitudinally from the lateral centerline 40 of the diaper 20 towards the front waist section 22 of the diaper 20 and the remainder extends longitudinally towards the rear waist section 24 of the diaper 20.

Desirably, the multilayered containment barriers 60 are configured to maintain contact with the wearer during use to provide improved resistance to the explosive flow of fecal exudates which may occur due to the compressive forces exerted by the wearer while sitting. To reduce the effect of the compressive forces exerted by the wearer, the containment barriers 60 in the illustrated embodiments are laterally spaced apart such that, when the diaper is being worn by a wearer, a void space is created between the wearer's buttocks and the containment barriers 60 and absorbent body 36 of the diaper. The size of the void space is dependent upon the height and length of the containment barriers 60, the lateral distance between the inner edges 70 of the containment barriers 60, and the compression resistance of the containment barriers 60 in use. Thus, the design and configuration of the containment barriers 60 is important to ensure that the void space between the containment barriers 60 is sufficient for containing the fecal exudates while not being too great that the wearer's buttocks push between the containment barriers 60 thereby exerting compressive forces on the fecal exudates.

For example, in the illustrated embodiments, the inner edges 70 of the containment barriers 60 may be laterally spaced apart a distance of from about 2 to about 10 centimeters, desirably no more than about 8 centimeters and more desirably no more than about 6 centimeters for improved performance. If the containment barriers 60 are positioned in a nonlinear or diverging configuration as illustrated in FIG. 3, it is particularly important to maintain such a distance between the containment barriers 60 in at least the portion of the diaper 20 intended to contact the buttocks of the wearer in use. This portion generally may extend from about 5 to about 15 centimeters in length longitudinally from the lateral centerline 40 of the diaper towards the rear waist section 24 of the diaper 20. In such a configuration, the multilayered containment barriers 60 are typically located at least partially on top of the absorbent body 36 of the diaper 20 near the longitudinal sides of the absorbent body 36. Alternatively, if the width of the absorbent body 36 is fairly narrow in the intermediate section 26 of the diaper 20, the containment barriers 60 may extend laterally beyond the longitudinal sides of the absorbent body 36. Generally, it is desirable that at least the inner edges 70 of the containment barriers 60 are located on the absorbent body 36 such that any fecal exudates contained in the void space between the wearer's body and the containment barriers 60 and the absorbent body 36 of the diaper 20 may be absorbed or desorbed by the absorbent body 36 or the individual layers 68 of the containment barriers 60.

The multilayered containment barriers 60 may have any shape which provides the desired void space between the wearer's buttocks and the absorbent body 36 of the diaper 20, inhibition of the flow of fecal exudates and containment and absorption of body exudates. Suitable cross sections for the multilayered containment barriers 60 include circular, semi-circular, oval, elliptical, triangular, rectangular, square, pyramidal, and the like. Desirably, the body facing edges of the containment barriers 60 are curved to reduce irritation and provide improved comfort to the wearer. The surfaces of the containment barriers 60 may also have any desired contour or configuration such as angled, sinusoidal, or egg carton shaped.

In the illustrated embodiments, each containment barrier 60 generally defines a length 62, a width 64, a height 66, and an inner 70 and outer edge 72. As used herein, the term "length" for each containment barrier 60 refers to the overall length of the barrier in the longitudinal direction. As discussed above, the length 62 and height 66 of the containment barriers 60 along with the lateral spacing between the barriers are important because they define the void space created to contain the fecal exudates. Desirably, the area of the void space is maximized while the height 66 of the containment barriers 60 is minimized to provide sufficient void volume while not causing excessive discomfort to the wearer.

In the illustrated embodiments, the length 62 of the multilayered containment barriers 60 must be sufficient to block at least the majority of the passageways out the side edges 28 of the diaper through which the fecal exudates may flow. Desirably, the length 62 of the containment barriers is at least sufficient to block the lateral flow of fecal exudates from the target zone of the diaper 20. For example, on a diaper article intended to be worn by a medium sized infant, the multilayered containment barriers 60 may define a length 62 of at least about 3 centimeters and desirably at least about 7 centimeters. Desirably, the containment barriers 60 define a length 62 which is at least about 15 percent of the length of the diaper 20 as measured along the longitudinal centerline 38 of the diaper 20. In a particular embodiment, the containment barriers 60 define a length which is equal to about 25 percent of the length of the diaper 20 as measured along the longitudinal centerline 38 of the diaper 20 for improved performance.

The length in the longitudinal direction of each layer 68 in the containment barrier 60 may also vary. For example, the length of the layer 68 which is intended to contact the wearer may be shorter or longer than the length of the layer intended to face the other portions of the diaper 20 or any intermediate layer. In a particular embodiment, the length of the layers 68 of the containment barrier 60 are configured in a descending stair step manner such that length of the layer 68 intended to contact the wearer is the smallest and the length of the layer facing the rest of the diaper is the greatest for improved stability and performance.

As representatively illustrated in FIGS. 1 and 3, the containment barriers 60 may be located along the side edges 28 of the diaper such that about one third of their length extends longitudinally from the lateral centerline 40 of the diaper 20 towards the front waist section 22 of the diaper 20 and the remainder extends longitudinally towards the rear waist section 24 of the diaper 20. Desirably, at least about 50 percent and more desirably from about 60 to about 80 percent of the length 62 of the containment barriers 60 is located rearward of the lateral centerline 40 of the diaper 20 for improved performance. As used herein, the term "rearward" relates to the direction extending from the lateral centerline 40 towards the rear waist section 24 of the diaper 20. For example, the containment barriers 60 may extend longitudinally from the lateral centerline 40 of the diaper 20 towards the front waist section 22 of the diaper 20 a length of from about 1 to about 5 centimeters and the from the lateral centerline 40 of the diaper 20 towards the rear waist section 24 of the diaper 20 a length of from about 5 to about 14 centimeters.

The height 66 of the multilayered containment barriers 60 must be sufficient to provide the desired void space between the wearers buttocks and the absorbent body 36 of the diaper 20 and the desired seal against the body of the wearer to resist the flow of fecal exudates even when the diaper is subjected to compressive forces by the wearer.

However, excessive height 66 of the containment barrier 66 may undesirably result in irritation and redmarking of the skin of the wearer. Desirably, the containment barriers 60 define an uncompressed height 66 of from about 0.3 to about 2.5 centimeters, more desirably at least about 0.5 centimeters and even more desirably at least about 0.75 centimeters for improved performance.

In the illustrated embodiments, the containment barriers 60 may be constructed such that the height of the inner edge 70 of the barrier 60 is less than the height of the outer edge 72 of the containment barrier 60. In the illustrated embodiments, as used herein, reference to the "inner edge" of the containment barriers 60 refers to the longitudinally extending side edge of the containment barriers closest to the longitudinal centerline 38 of the diaper 20 while reference to the "outer edge" of the containment barriers 60 refers to the longitudinally extending side edge of the containment barriers located laterally outwards from the inner edge 70 and more distant from the longitudinal centerline 38 of the diaper 20 than the inner edge 70. Slanting the bodyfacing surface of the containment barriers 60 in such a manner provides improved comfort for the wearer by better conforming to the buttocks of the wearer. In such a configuration, it remains desirable that the height of the inner edge 70 of the containment barriers 60 be at least about 0.5 centimeters to effectively provide the desired void space between the buttocks of the wearer and the absorbent body 36 of the diaper 20.

The width 64 of the containment barriers 60 provides stability to the barriers 60 such that they do not fold over or bend during use. For example, the multilayered containment barriers 60 define an overall width 64 of from about 0.5 to about 2.5 centimeters, desirably at least about 0.6 centimeters and more desirably at least about 1.0 centimeters for improved performance. Desirably, the containment barriers 60 define a width 64 which is at least about 7 percent of the width of the diaper 20 as measured along the lateral centerline 40 of the diaper 20. In a particular embodiment, the containment barriers 60 define a width 64 which is equal to about 16 percent of the width of the diaper 20 as measured along the lateral centerline 40 of the diaper 20 for improved performance. Widths less than those set forth above may undesirably result in instability of the barrier and irritation of the skin of the wearer during use while widths greater than those set forth above may undesirably result in a diaper having a wide crotch portion which may adversely affect fit and performance.

The width in the lateral direction of each layer 68 in the containment barrier 60 may also vary. For example, the width of the layer 68 which is intended to contact the wearer may be less than or greater than the width of the layer intended to face the other portions of the diaper 20 or any intermediate layer. In a particular embodiment, the width of the layers 68 of the containment barrier 60 are configured in a descending stair step manner such that width of the layer 68 intended to contact the wearer is the smallest and the width of the layer facing the rest of the diaper is the greatest for improved stability and performance. In an alternative configuration, the width of the layers 68 of the containment barrier 60 may be configured in a stair step manner such that width of the layer 68 intended to contact the wearer is the greatest and the width of the layer facing the rest of the diaper is the smallest. In such a configuration, the distance between the inner edges 70 of the bodyfacing layer of the containment barriers 60 is less than the distance between the inner edges 70 of the diaper facing layer of the containment barriers 60 in a shelf-like manner for improved containment of exudates.

To maintain the stability of the containment barriers 60 during use, the containment barriers 60 define a width to height ratio of at least about 0.5, desirably at least about 0.75, and more desirably at least about 1.0. Width to height ratios less than those set forth above may undesirably result in the containment barriers 60 bending or folding over which reduces the void space between the wearer's body and the absorbent body 36 and results in increased flow of fecal exudates over the barriers 60.

In one embodiment of the present invention, the containment barriers 60 may be held or anchored in place to improve the stability of the containment barriers by one or more sheets of material such as a nonwoven material or foam material which extends at least partially over the bodyfacing surface of the containment barriers 60 and which may be attached to the topsheet 34 or absorbent body 36 of the diaper 20. The use of such material to anchor the barriers in place can help minimize the required width to height ratio for maintaining the stability of the barriers. Desirably, the sheet of material conforms to the shape and contour of the containment barriers 60 to prevent any gaps from forming between the sheet of material and the containment barriers 60. For example, the sheet of material may be adhesively bonded to the outer surface of the containment barriers 60 to prevent such gaps. It is further desirable that the sheet of material surround and secure at least three of the sides of the containment barriers 60 for improved stability. The sheet or sheets of material may be provided by any material which is relatively soft and strong to anchor the barriers 60 in place and provide a cushion between the barriers 60 and the body of the wearer. Desirably, the sheet of material is a hydrophobic material such that the sheet is not configured to assist in drawing the fecal exudates over the top of the barriers 60.

As representatively illustrated in FIGS. 1 and 2, the containment barriers 60 of the different aspects of the present invention may also include an inner edge 70 which is nonlinear in shape for improved performance. Such a curvilinear shape for the inner edge 70 of the containment barriers 60 is described in commonly assigned U.S. patent application No. 08/763,960, filed Dec. 5, 1996, in the name of Barbara O. Sauer and entitled "ABSORBENT ARTICLE HAVING THREE DIMENSIONAL LONGITUDINAL CONTAINMENT BARRIERS," the disclosure of which is hereby incorporated by reference. For example, the inner edge 70 of the containment barriers 60 may have a sinusoidal, stair step, ladder, or V notched shape as are well known to those skilled in the art. Alternatively, as representatively illustrated in FIGS. 3 and 4, the containment barriers 60 may define inner edges 70 which are linear and which may or may not diverge from each other.

It is also desirable that the containment barriers 60 be flexible such that they readily conform to the shape and contours of the wearer's buttocks. If the flexibility of the containment barriers 60 is too low, the containment barriers may not effectively conform to the body of the wearer and may cause undesired leakage and redmarking and irritation of the skin of the wearer.

The containment barriers 60 of the different aspects of the present invention include multiple layers 68 for improved absorption and containment of body exudates. For example, to provide such improved absorption and containment, each containment barrier 60 includes at least 3, desirably at least about 5 and more desirably at least about 8 individual layers 68 of material. The layers 68 are arranged and suitably connected together such that the inner edges 70 of the layers are free to move relative to each other to readily space apart to accept body exudates. Such spacing creates additional surface area on the containment barrier 60 for absorbing exudates thereby providing improved absorption and containment. As discussed above, the layers 68 may be of the same or different shape, size or material and may be oriented in a parallel or perpendicular relationship with the bodyfacing surface of the diaper 20. For example, the layers 68 intended to contact the wearer may be of different height, length, width or material than the layers intended to attach the barrier to the diaper 20.

Figure 5:
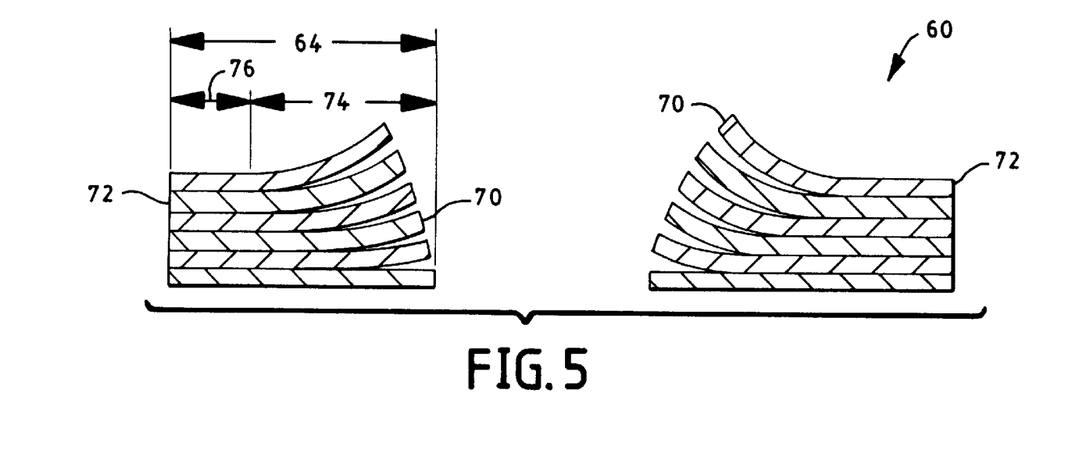
FIG. 5 representatively shows a sectional view of the containment barriers of the absorbent article of FIG. 3 taken along line 4—4 wherein the separate layers of the barrier are shown in a flared out condition simulating there configuration during use.

As representatively illustrated in FIG. 5, each layer 68 may define an inner edge 70 which remains at least partially unattached to the other layers and an outer edge 72 which is at least partially attached to the other layers 68. Since the inner edge 70 of each layer is not attached to the other layers 68, the inner edge 70 is allowed to flare upwards in use to create a gap between the layers 68 as illustrated in FIG. 5. Such a gap allows body exudates to flow and wick between the layers and be contained or absorbed by the layers. To facilitate this flaring or spacing, the layers 68 may include a longitudinally extending bend or crease therein which allows them to more readily bend or flex upwardly. Moreover, it has been discovered that inner edge of layers 68 made from a relatively stiff material may flex or bend upwardly more readily when the containment barrier 60 is subjected to compression forces by the wearer at a position laterally outward from the inner edge.

The numerous layers 68 of each containment barrier 60 may be attached together using methods described above as being suitable for attaching other components of the diaper 20 together such as adhesive bonding or ultrasonic bonding. The layers 68 may be attached together along any portion thereof which provides the desired gapping or spacing between the inner edges 70 of the layers 68 for improved absorption of exudates. For example, as representatively illustrated in FIG. 5, the layers 68 are at least partially attached together along there outer edges 72 but remain unattached at their inner edges 70 such that they define an unattached width 74 and an attached width 76. For improved performance, the layers 68 desirably define an unattached width 74 extending from the inner edge 70 which is at least about 10 percent and more desirably from about 30 to about 80 percent of the width 64 of the containment barrier 60. In such a configuration, the body exudates readily flow in between the layers 68 along the inner edges 70 thereof for improved containment, distribution and absorption.

The multilayered containment barriers 60 are configured to maintain their shape during use to effectively provide the void space between the wearers buttocks and the absorbent body 36 of the diaper 20 and inhibit the lateral flow of fecal exudates. For example, it is desirable that the containment barriers 60 be capable of resisting any z-directional compressive forces which may be exerted by the wearer during use. In a particular embodiment, the containment barriers 60 define a z-directional compression resistance of at least about 50 percent, desirably at least about 70 percent, and more desirably at least about 85 percent. For example, the containment barriers 60 may define a compression resistance of from about 50 to about 95 percent When the containment barriers have a compression resistance less than the values set forth above, the containment barriers may collapse during usage which adversely affects the ability of the barriers to provide the desired void space and resist the lateral flow of fecal exudates. Whereas, if the compression resistance of the containment barriers is too high, the containment barriers may cause undesired redmarking and irritation of the skin of the wearer.

Desirably, the containment barriers 60 have sufficient compression resilience such that the height 66 of the barriers 60 remains at least about 0.3 centimeters and desirably at least about 0.5 centimeters when the containment barriers 60 are under a compressive load of about 350 grams per square centimeter.

The layers 68 of the containment barriers 60 of the different aspects of the present invention, as representatively illustrated in FIGS. 1–5, may be made from any material which provides the desired containment and level of compression resistance. Suitable materials include layers of foams, fibrous webs of natural or synthetic fibers or combinations thereof, and multiple layer fibrous webs. For example, the individual layers 68 of the containment barriers 60 may be a crosslinked polyethylene foam material which is commercially available from Sentinel Foams, a business having offices located in Hyannis, Massachusetts, under the trade designation EMR NAT. The layers 68 may otherwise include an open celled polyester based foam material commercially available from Woodbridge Foam Fabricating, Incorporated, a business having offices located in Chattanooga, Tenn., under the trade designation SM-25 BIOFREE ELASTICIZED FOAM. Such foam materials may be particularly desirable since they act like a sponge upon compression and release from the wearer to improve the absorption of exudates.

Alternatively, the layers 68 of the containment barriers 60 may be provided by nonwoven materials such as a hydroentangled nonwoven material commercially available from E. I. Dupont de Nemours under the trade designation SONTARA 8423. Other suitable woven and nonwoven fabrics can be used to construct containment barriers 60. For example, the containment barriers 60 may include layers 68 composed of a meltblown or spunbonded web of polyolefin fibers, or a bonded-carded-web or an airlaid web composed of natural and synthetic fibers. The bonded-carded-web may, for example, have a basis weight of about 84 grams per square meter and include bicomponent fibers such as bicomponent fibers having a polyethylene sheath and a polyester core. Such woven and nonwoven materials may be treated with a surfactant or otherwise processed to impart a desired level of wettability and hydrophilicity. Similar to the foam materials, the nonwoven materials may also perform like a sponge upon compression and release from the wearer to improve the absorption of exudates. Desirably, at least one and more desirably the majority of the layers 68 of each containment barrier 60 are capable of absorbing body exudates for improved absorption and leakage reduction.

The different layers 68 of the containment barriers 60 may also be provided by different materials which provide different physical properties. For example, in a particular embodiment, the containment barriers 60 may include a top layer which is configured to provide a soft, gentle contact with the wearer's buttocks. In such a configuration, the other layers may be configured to provide the desired absorption and containment of exudates and the compression resistance to effectively provide the void space between the wearer's buttocks and the absorbent body 36 of the diaper 20 and inhibit the flow of such exudates. The top layer in such a configuration may be constructed of a nonwoven or foam material as described above as being suitable for the topsheet or similar materials known to those skilled in the art while the other layers may be constructed of any suitable material having the desired compression resistance and/or absorption. The top layer of the containment barrier 60 may also be hydrophobic to repel exudates and maintain a cleaner appearing top surface in contact with the skin of the wearer.

As representatively illustrated in FIGS. 1 and 2, the diaper 20 of the different aspects of the present invention may also include a pair of elasticized, longitudinally-extending containment flaps 80. The containment flaps 80 are configured to maintain an upright, perpendicular arrangement in at least the intermediate section 26 of the diaper 20 to serve as an additional barrier to the lateral flow of body exudates. In the illustrated embodiment, a pair of containment flaps 80 are attached to the topsheet 34 of the diaper 20 along the side edges 28 of the diaper 20. Suitable arrangements and constructions for containment flaps 80 are described, for example, in U.S. Pat. No. 4,704,116 issued Nov. 3, 1987, to K. Enloe, the disclosure of which is hereby incorporated by reference to the extent it is consistent herewith.

The containment flaps 80 are attached to the topsheet 34 along attached edges 94. The containment flaps 80 also include free edges 92 which are configured to remain unattached to the other components of the diaper 20 in at least the intermediate section 26 of the diaper 20. The free edges 92 of the containment flaps 80 include a flap elastic member 86 which can comprise one or more strands of individual elastic material.

For example, a suitable elastic strand may be composed of a 470 decitex LYCRA elastomer which is available from E. I. DuPont de Nemours. The elastic member 86 is connected to the free edge 82 in an elastically contractible condition such that the contraction of the elastic member 86 contracts and gathers the free edge 82. As a result, the free edge 82 of the containment flaps tends to position itself in a spaced relation away from the topsheet 34 of the diaper 20 toward a generally upright and approximately perpendicular configuration, especially in the intermediate section 26 of the diaper 20.

As representatively illustrated in FIGS. 1 and 2, the containment flaps 80 are desirably located along the side edges 28 of the diaper 20 laterally outwards from the containment barriers 60 for improved containment of body exudates and, in particular, fecal exudates. In such a configuration, it is desirable that, in an unrestrained configuration, the containment flaps 80 extend in a generally perpendicular manner above the containment barriers 60 a distance of at least about 0.2 centimeters and more desirably at least about 1.0 centimeters for improved containment of body exudates. The existence of the containment barriers 60 in the diaper of the present invention allows the containment flaps 80 to extend a greater distance than conventional containment flaps because the containment barriers 60 prevent at least a portion of the containment flaps 80 from folding inwardly and overlapping with each other. The containment flaps 80 may also be located laterally outward from the barriers 60 to provide additional void space between the flaps 90 and the outer edges of the barriers 60.

In the various aspects of the invention, the containment flaps may be constructed of a fibrous material which is similar to those materials described as being suitable for the topsheet 34. Other conventional films such as polymeric films may also be employed. In the illustrated embodiment, the containment flaps 80 are constructed of a spunbond-meltblown-spunbond laminate material composed of polypropylene fibers and having a basis weight of about 25 grams per square meter.

In another embodiment of the invention as representatively illustrated in FIGS. 3 and 4, the containment barriers 60 may be located between the topsheet 34 and the absorbent body 36 of the diaper 20. In such a configuration, the topsheet 34 may extend at least partially over the containment barriers 60 and include an opening 110 therein which is configured to receive fecal exudates. The opening 54 is located such that the fecal exudates pass through the opening 54 and into the void space created by the containment barriers 60.

The opening 54 in the topsheet 34 generally defines a length in the longitudinal direction and a width in the lateral direction. The length and width of the opening 54 must be sufficient to allow fecal exudates to pass through into the void space created between the containment barriers 60. Desirably, the size of the opening 54 is not too large such that the area of the topsheet 34 surrounding the opening 54 prevents excessive contact of the body exudates contained within the diaper 20 with the skin of the wearer. Thus, the dimensions of the opening 54 may be controlled to provide improved skin wellness of the wearer.

Desirably, the opening 54 in the topsheet 34 is similar in size to the target zone of the diaper 20. For example, the opening 54 may define an open area of at least about 5 square centimeters and desirably from about 20 to about 50 square centimeters. On a diaper article intended to be worn by a medium sized infant, the opening may define a length along the longitudinal centerline 38 of the diaper 20 of at least about 4 centimeters and desirably at least about 7 centimeters and a width as measured along the lateral centerline 40 of the diaper 20 of from about 1.0 to about 10 centimeters and desirably from about 2.5 to about 7.5 centimeters. Desirably, the opening 54 defines a length along the longitudinal centerline 38 which is at least about 20 percent of the length of the diaper 20 as measured along the longitudinal centerline 38 of the diaper 20 and a width which is at least about 20 percent of the width of the diaper 20 as measured along the lateral centerline 40 of the diaper 20 for improved performance.

As representatively illustrated in FIGS. 3 and 4, the opening 54 in the topsheet 34 is desirably located such that about one third of it's length extends longitudinally from the lateral centerline 40 of the diaper 20 towards the front waist section 22 of the diaper 20 and the remainder extends longitudinally towards the rear waist section 24 of the diaper 20. Desirably, at least about 50 percent and more desirably from about 60 to about 70 percent of the length of the opening 54 is located rearward of the lateral centerline 40 of the diaper 20 for improved performance.

The opening 54 may have any shape which is capable of receiving the fecal exudates. Suitable shapes include circular, oval, elliptical, square, rectangular and the like. In a particular embodiment as representatively illustrated in FIG. 3, the laterally opposed side edges of the opening 110 diverge from each other laterally outward in the rear waist section 24 of the diaper 20. Such a configuration has been found to better fit the buttocks of the wearer which may provide improved reception and containment of the fecal exudates.

As representatively illustrated in FIGS. 3 and 4, the topsheet 34 in such a configuration may include at least one elastic member 56 which can comprise one or more strands of individual elastic material. For example, a suitable elastic strand may be composed of a 470 decitex LYCRA elastomer which is available from E. I. DuPont de Nemours. The elastic member 56 may be connected to the edge of the opening 54 in the topsheet 34 in an elastically contractible condition such that the contraction of the elastic member 56 contracts and gathers the topsheet 34. Desirably, as illustrated in FIGS. 3 and 4, the topsheet 34 includes an elastic member 56 at least along both of the laterally opposed side edges of the opening 54 in the topsheet 34. In such a configuration, the elastic member 56 can assist in providing a close conforming fit between the topsheet 34 and the buttocks of the wearer which results in improved location of the opening over the anus of the wearer to better receive fecal exudates.

Accordingly, the different aspects of the present invention advantageously provide an absorbent article having improved containment and control of body exudates and, in particular, fecal material. The multilayered containment barriers of the present invention are configured to absorb and contain at least a portion of the body exudates. In addition, the containment barriers are resistant to compression and flexible to effectively provide a void space between the buttocks of the wearer and the absorbent body of the article and inhibit the lateral flow of fecal exudates. As a result, absorbent articles made according to the present invention may have a reduced incidence of leaks in the leg and waist regions of the article.

The different aspects of the present invention may also include a pair of longitudinally extending containment flaps in combination with the multilayered containment barriers to further reduce the incidence of leaks. Moreover, the topsheet or bodyside liner of the article of the present invention may be configured to conform to the buttocks of the wearer to better isolate the body exudates from the wearer. In such a configuration, the topsheet of the article includes an opening which is configured to allow fecal exudates to pass through the topsheet and into the void space between the wearer's buttocks and the containment barriers and absorbent body of the article.

Compression Resistance Test

This test is configured to measure the compression resistance of materials intended for use as the containment dam according to the present invention. The compression resistance of the materials indicates the ability of the material to maintain it's shape during use.

A sample of a containment barrier according to the present invention is obtained. The compression resistance of the sample is tested in a standard compressometer such as that commercially available from Frazier Precision Instrument Company, a business having offices located in Gaithersburg, Maryland. Initially, the compressometer is calibrated. The sample is then placed in the compressometer which includes a foot which defines a diameter of 3.0 inches. The foot is positioned in contact with the sample and the original height of the sample is measured and recorded. The foot is then lowered until the pressure on the sample is 1.0 pounds per square inch. The compressed height of the sample is immediately measured and recorded. The compression resistance value of the sample is then obtained by dividing the compressed height by the original height and multiplying the result by 100 percent.

The following Examples are presented to provide a more detailed understanding of the invention. The Examples are intended to be representative, and are not intended to limit the scope of the invention.

EXAMPLES

Diapers which included two longitudinally extending containment barriers along the side edges of the diaper were placed on 15 infants. The diapers were substantially identical to the diapers representatively illustrated in FIGS. 3 and 4. Each diaper included one multilayered containment barrier along one side edge and one single-layered containment barrier along the opposite side edge.

Both of the barriers were manufactured from an open-celled polyester based foam material commercially available from Woodbridge Foam Fabricating, Incorporated under the trade designation SM-25 BIOFREE ELASTICIZED FOAM. Each containment barrier defined a width of 3 centimeters, a length of 12.7 centimeters, and a height of about 0.5 inches under a pressure of 78.5 grams per square inch. The multilayered barrier included 7 layers which were attached to each other using 0.25 inch wide two sided adhesive tape commercially available from 3M Company under the trade designation Y948 placed adjacent the outer edge of the barrier. Thus, the barrier defined an unattached width of 60 percent of the total width of the barrier. The containment barriers were attached to the diaper using a single bead of an adhesive commercially available from Ato-Findley, Incorporated under the trade designation H2096 for easy removal. The barriers were weighed with the adhesive thereon before being inserted into the diaper.

The diapers were placed on the 15 infants and the infants wore the diapers until they had a bowel movement. If, after 4 hours, the infant did not have a bowel movement, 60 cubic centimeters of cream corn were injected into the diaper. After use, the diapers were removed from the infants and the containment barriers were removed from the product and reweighed. One of the diapers was not considered because the bowel movement was very hard. The difference in weights of the containment barriers in the remaining 14 diapers defined the amount of exudates or cream corn contained within the barrier. The multilayered containment barriers contained an average of 2.32 grams of exudates or cream corn. The solid, single-layered containment barriers contained an average of 1.91 grams of exudates or cream corn. Thus, on average, the multilayered containment barrier contained 20 percent more than the single-layered containment barrier.

Having thus described the invention in rather full detail, it will be readily apparent to a person of ordinary skill that various changes and modifications can be made without departing from the spirit of the invention. All of such changes and modifications are contemplated as being within the scope of the present invention as defined by the subjoined claims.

I claim:

1. A disposable absorbent article having a front waist section, a rear waist section, an intermediate section which interconnects said front and rear waist sections, a pair of longitudinally opposed end edges, and a pair of laterally opposed side edges, said article comprising at least one multilayered containment barrier which is located adjacent one of said edges of said absorbent article to inhibit the flow of body exudates and which comprises at least three layers of material configured in a facing relationship with each other and extending in a parallel relationship with a bodyfacing surface of said article in use wherein each of said layers defines an outer edge which is attached to said other layers and a free edge which remains at least partially unattached to said other layers to allow said body exudates to flow into an area between said layers in use.

2. An absorbent article according to claim 1 wherein said containment barrier includes at least about 8 of said layers of material.

3. An absorbent article according to claim 1 wherein said containment barrier includes at least about 5 of said layers of material.

4. An absorbent article according to claim 1 wherein each of said layers of said containment barrier defines an unattached width wherein said laver of said containment barrier is not attached to any of said other layers of said containment barrier which is at least about 10 percent of a width of said containment barrier.

5. An absorbent article according to claim 1 wherein each of said layers of said containment barrier defines an unattached width wherein said laver of said containment barrier is not attached to any of said other layers of said containment barrier which is from about 30 to about 80 percent of a width of said containment barrier.

6. An absorbent article according to claim 1 wherein said layers of material are hydrophilic.

7. An absorbent article according to claim 1 wherein said layers of material comprise a bonded carded web material.

8. An absorbent article according to claim 1 wherein said containment barrier defines a width to height ratio of at least about 0.5.

9. An absorbent article according to claim 1 wherein said containment barrier defines a compression resistance of at least about 50 percent as determined according to a Compression Resistance Test set forth herein.

10. A disposable absorbent article having a front waist section, a rear waist section, an intermediate section which interconnects said front and rear waist sections, a pair of longitudinally opposed end edges, and a pair of laterally opposed side edges, said article comprising:
 a) a backsheet layer;
 b) a liquid permeable topsheet layer which is connected in superposed relation to said backsheet layer;
 c) an absorbent body which is located between said topsheet layer and said backsheet layer, and
 d) a pair of longitudinally extending, multilayered containment barriers which are located in a laterally spaced apart relation on said topsheet layer of said absorbent article and which are configured to provide a void space between a wearer's buttocks and said topsheet layer of said absorbent article for containing body exudates wherein each of said containment barriers includes at least 3 layers of material configured in a facing relationship with each other and extending in a parallel relationship with a bodyfacing surface of said article in use and wherein each of said layers of said containment barrier defines an outer edge which is attached to said other layers of said containment barrier and an inner edge which remains at least partially unattached to said other layers of said containment barrier to allow said body exudates to flow into an area between said layers of said containment barrier in use.

11. An absorbent article according to claim 10 wherein each of said containment barriers includes at least about 5 of said layers of material.

12. An absorbent article according to claim 10 wherein each of said layers of said containment barriers defines an unattached width wherein said layer of said containment barrier is not attached to any of said other layers of said containment barrier which is at least about 10 percent of a width of said containment barrier.

13. An absorbent article according to claim 10 wherein each of said layers of said containment barriers defines an unattached width wherein said layer of said containment barrier is not attached to any of said other layers of said containment barrier which is from about 30 to about 80 percent of a width of said containment barrier.

14. An absorbent article according to claim 10 wherein at least one of said layers of material in each of said containment barriers is hydrophilic.

15. An absorbent article according to claim 10 wherein said layers of material comprise a bonded carded web material.

16. An absorbent article according to claim 10 wherein each of said containment barriers defines a width to height ratio of at least about 0.5.

17. An absorbent article according to claim 10 wherein each of said containment barriers defines a length of at least about 15 percent of a length of said article and wherein at least about 50 percent of said length of each of said containment barriers is located rearward of a lateral centerline of said absorbent article.

18. An absorbent article according to claim 10 wherein each of said containment barriers defines a compression resistance of at least about 50 percent as determined according to a Compression Resistance Test set forth herein.

19. An absorbent article according to claim 10 and further comprising a pair of longitudinally extending containment flaps which are located along said side edges of said absorbent article laterally outwards from said containment barriers and which define an attached edge which is at least partially attached to said side edges of said absorbent article, a free edge which remains unattached to said side edges in at least said intermediate section of said absorbent article, and at least one elastic member which is configured to maintain said free edge in a generally perpendicular, spaced away relationship from said side edge of said absorbent article in said intermediate section.

20. An absorbent article according to claim 19 wherein said free edge of each of said containment flaps is configured to extend in a generally perpendicular manner above said containment barriers a distance of at least about 0.2 centimeters.

* * * * *